United States Patent [19]

Edwardson

[11] Patent Number: 4,571,184

[45] Date of Patent: Feb. 18, 1986

[54] IMPLEMENT FOR ABRASION
[75] Inventor: Svante R. Edwardson, Solna, Sweden
[73] Assignee: AB Dentatus, Hagersten, Sweden
[21] Appl. No.: 491,966
[22] PCT Filed: Sep. 9, 1982
[86] PCT No.: PCT/SE82/00277
    § 371 Date: Apr. 19, 1983
    § 102(e) Date: Apr. 19, 1983
[87] PCT Pub. No.: WO83/00824
    PCT Pub. Date: Mar. 17, 1983

[30] Foreign Application Priority Data

Sep. 10, 1981 [SE] Sweden ................................. 8105396

[51] Int. Cl.⁴ .............................................. A61C 3/06
[52] U.S. Cl. ..................................................... 433/166
[58] Field of Search .................... 51/206 R; 125/15;
                76/DIG. 4, 101 A, 101 R; 433/125, 166

[56] References Cited

U.S. PATENT DOCUMENTS

| | | | |
|---|---|---|---|
| 1,791,968 | 2/1931 | Morgan | 76/101 A |
| 2,645,471 | 7/1953 | King | 76/101 A |
| 3,496,973 | 2/1970 | Ballard | 125/15 |
| 3,553,905 | 1/1971 | Lemelson | 125/15 |
| 4,353,696 | 10/1982 | Bridges | 433/125 |

FOREIGN PATENT DOCUMENTS 1152208 1/1963 Fed. Rep. of Germany .
313482 8/1969 Sweden .

Primary Examiner—Harold D. Whitehead
Attorney, Agent, or Firm—Young & Thompson

[57] ABSTRACT

A dental implement for abrasion, comprising a steel spatula coated on its opposite broad surfaces with an abrasive coating of tungsten applied to the steel surfaces with the aid of an electric arc. The implement is particularly useful for dentistry, because the tungsten has very little effect on the relatively hard tooth enamel but is quite abrasive on such dental materials as gold, amalgam, and dentine. Thus the implement is especially suited to smoothing tooth fillings of various types where the tooth enamel is to be left intact but the foreign material is to be evened out to make as smooth a transition as possible to the surrounding tooth enamel.

1 Claim, 3 Drawing Figures

FIG. 1
FIG. 2
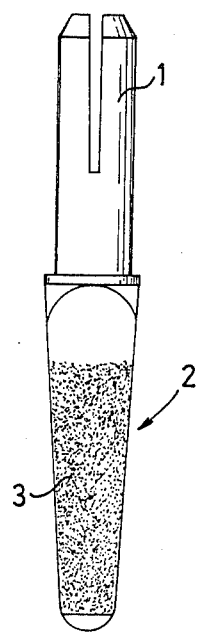
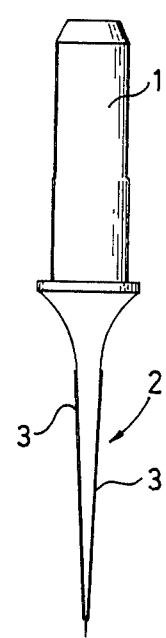

IMPLEMENT FOR ABRASION

BACKGROUND OF THE INVENTION

It is previously known to provide metal surfaces with a hard surface layer of another metal applied with the aid of an electric arc. Steel surfaces provided with surface layers of tungsten applied in this manner have for example been used in connection with rollers and die cutting tools. The surface layers, after surface treatment such as grinding and/or polishing, by virtue of their hardness or wear strength, are employed as the wear surfaces on the rollers and the cutting edges on the dies.

SUMMARY OF THE INVENTION

The present invention is based on the observation, made in connection with the known practice of applying a surface layer of another metal to metal surfaces by means of an electric arc, that such surface layers are, if the usual grinding and/or polishing thereof is omitted, not only surprisingly usable but even quite suitable as abrasive means. This has especially proved true in the field of dentistry, since tests with surface layers of this type have shown them to have very little effect on the relatively hard tooth enamel but are quite abrasive on such dental materials as gold, amalgam and the tooth's own bone substance (dentin). In other words, they are especially suited to smoothing tooth fillings of various types where the tooth enamel is to be left intact but the foreign material is to be evened out to make as smooth a transition as possible to the surrounding tooth enamel.

More specifically, implements for abrasion made according to the invention have proved to fulfill a previously unmet need within the field of dentistry. They have almost completely complemented the previously available implements of rubber and plastic used together with abrasive paste, and the implements of steel which are provided with diamond coatings. The rubber and plastic implements used together with abrasive paste are less rigid and wear-resistant and in many cases have insufficient abrasion but provide a very smooth surface, and the diamond-coated steel implements are many times much too abrasive leaving a rough surface. The implements made according to the invention with surface coatings or another metal applied with the aid of an electric arc, in addition to holding their shape and having a long life, also have an abrasive capacity lying between the two previously-mentioned types of implements, i.e. a comparatively good cutting capacity while providing a high surface finish on the tooth surface.

Even in comparison with steel implements such as ordinary files, the implements made according to the invention with surface layers of another metal applied by means of an electric arc have proved to be superior both as regards cutting capacity and life as well as high surface finish on the tooth surfaces.

Even if the stated examples of advantages with the implements made according to the invention for abrasion have been taken from the field of dentistry, the invention is not of course limited to this field but is generally applicable to other fields using abrasion, for example precious metals, metal alloys of various types, hardwoods, bone etc.

As has been stated above, an implement made according to the invention for abrasion and comprising a metal portion, provided at least partially with an abrasive coating, is characterized primarily in that the abrasive coating consists of a hard surface layer of another metal material than that of the metal portion, applied to the metal portion with the aid of an electric arc. Using steel for the metal portion serving as a carrier of the abrasive coating, tungsten has proved to be an especially suitable material for the abrasive coating. For the actual coating process, commercially available equipment can be used. No subsequent working of the surface of the finished abrasive coating is required. On the contrary, it is to be left as it is when applied with the arc.

BRIEF DESCRIPTION OF THE DRAWINGS

The invention will be described in the following with reference to an example shown in the accompanying drawing of a suitable embodiment of an implement according to the invention for surface treatment of teeth.

FIGS. 1 and 2 show the appearance of this implement as seen from two different views, while

DETAILED DESCRIPTION OF THE INVENTION

Figure 3:
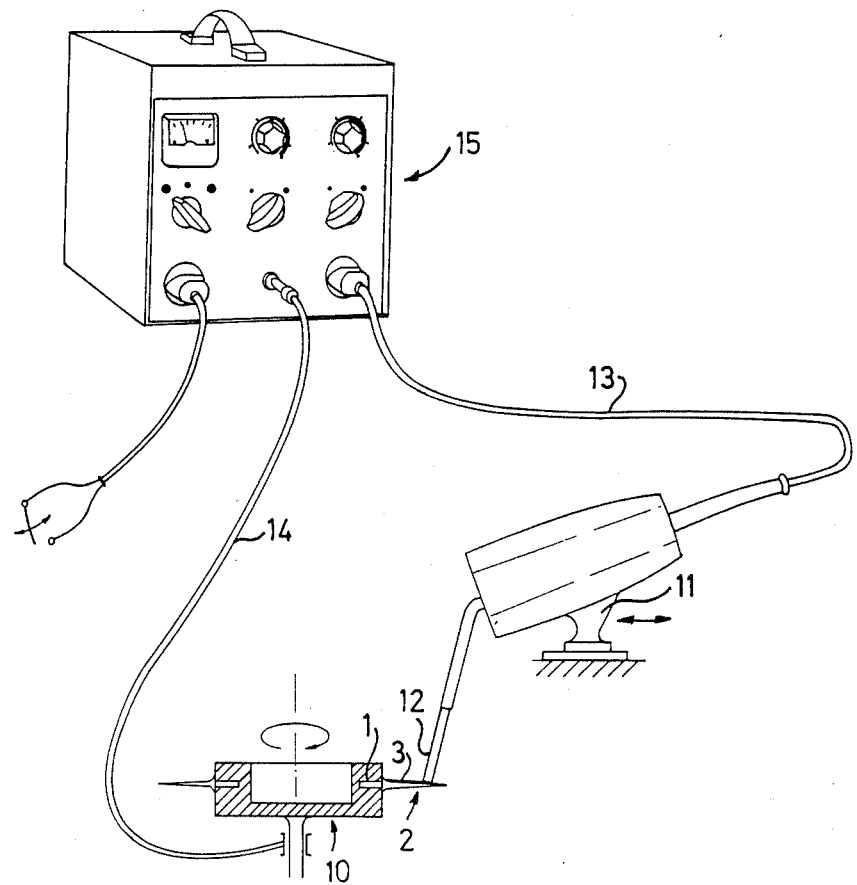
FIG. 3 shows quite schematically how the abrasive surface coating of the implement has been achieved.

The embodiment of the inventive implement shown in the drawing resembles most nearly a file and has a steel shank 1 for fixing the implement in known handles for dental purposes for imparting reciprocal movement to the implement. A thin spatula-like portion 2 extends axially from the steel shank 1 and is integral therewith, one or both broad sides thereof being provided with abrasive material intended for surface treatment of teeth. The spatula-like portion 2 has been made thin because the implement is intended to be used in the approximal spaces of the set of teeth.

In accordance with the invention, the abrasive material applied to the broad sides of the spatula-like portion with the aid of an electric arc consists of hard surface layers 3 of another material than steel, i.e. another metal material than that which the shank and the spatula portion of the implement are made of.

In the embodiment shown here, this other metal material is tungsten, since this material has been shown to be especially suitable in dental implements. Even other metal materials, which can be applied to a metal substrate with an electric arc, can be used however and should be suited to several other areas of use.

The application of the abrasive coating or surface layers 3 to the broad sides of the spatula portion 2 of the implement is suitably done as follows.

The main portion of the implement to be coated, which is of steel and is thus electrically conducting, is mounted with its shank 1 in a rotating holder 10, which advances gradually and at the right speed subsequent sections of the broad sides of the spatula portion 2 up to and past a tungsten carbide electrode 12 mounted on a support 11 for reciprocal movement. The electrode is mounted so that during reciprocation it will coat said broad side. Because both the tungsten carbide electrode 12 and the implement itself 1,2 are joined by electric conductors 13,14 to opposite poles in a circuit of an apparatus 15 of a type available on the market, an electric arc will be generated as soon as the electrode and the implement come into contact with each other. The heat generated will melt the tungsten from the electrode and melt it onto the exposed broad surface of the implement. When the required size of the surface layer has been achieved, the operation is ended by breaking the circuit.

The apparatus 15 used to create a suitable circuit can for example be of the type available on the market under the name TUCADOR ® 2000.

The invention is not limited to the example described here and shown in the drawing, but can be modified in many ways within the scope of the claim. For example, an implement made according to the invention can instead of being made for reciprocating work movements be made for rotating movements with the same advantages.

I claim:

1. A dental abrading implement comprising a shank means for connection to a handle means, a thin steel spatula connected to said shank means and having broad opposite sides, and on at least one of said broad sides a hard surface layer of tungsten applied to the steel with the aid of an electric arc whereby tooth enamel remains relatively unaffected during abrading.

* * * * *